(12) United States Patent
Chou et al.

(10) Patent No.: US 6,977,721 B2
(45) Date of Patent: Dec. 20, 2005

(54) FOREIGN SUBSTANCE INSPECTION APPARATUS

(75) Inventors: Hsin Tan Chou, Bah-Der (TW); Cheng Yu Chen, Bah-Der (TW); Taizo Yamamoto, 1-20-30, Sekime, Joto-ku, Osaka-shi, Osaka-fu (JP); Noboru Hoshi, Osaka (JP); Kohachi Kawamura, Osaka (JP)

(73) Assignees: Mingtai Chemical Co., Ltd., Bah-Der (TW); Nisshin Kasei Co., Ltd., Osaka (JP); Taizo Yamamoto, Osaka (JP)

( * ) Notice: Subject to any disclaimer, the term of this patent is extended or adjusted under 35 U.S.C. 154(b) by 213 days.

(21) Appl. No.: 10/622,777

(22) Filed: Jul. 21, 2003

(65) Prior Publication Data
US 2004/0085531 A1 May 6, 2004

(30) Foreign Application Priority Data
Jul. 22, 2002 (JP) ............................. 2002-212196

(51) Int. Cl.$^7$ .......................................... G01N 21/00
(52) U.S. Cl. ................................................ 356/237.1
(58) Field of Search ....................... 356/237.1–237.6, 356/36–38, 337–343; 73/866, 865.8, 865.5; 141/65–69, 141/130, 374; 222/405

(56) References Cited

U.S. PATENT DOCUMENTS

| 4,976,540 A | 12/1990 | Kitamura et al. ............. 356/38 |
| 5,157,976 A | 10/1992 | Tokoyama et al. ......... 73/865.8 |
| 5,239,358 A | 8/1993 | Tokoyama ................... 356/244 |
| 5,469,752 A * | 11/1995 | Kitamura et al. ............. 73/866 |
| 5,727,607 A * | 3/1998 | Ichikawa et al. ............. 141/67 |
| 6,454,141 B1 * | 9/2002 | Breen et al. ................ 222/405 |

FOREIGN PATENT DOCUMENTS

| JP | 7-48065 | 5/1995 |
| JP | 2000-146848 | 5/2000 |

OTHER PUBLICATIONS

Patent Abstracts of Japan; 09281048; publication date: Oct. 31, 1997, cited in search report (abstract only).

* cited by examiner

Primary Examiner—Tu T. Nguyen
(74) Attorney, Agent, or Firm—Armstrong, Kratz, Quintos, Hanson & Brooks, LLP

(57) ABSTRACT

A foreign substance inspection apparatus 1 which obtains images of a powder material with a two-dimensional camera 17 and subjects the image data outputted from the camera 17 to image processing, whereby foreign substances mixed into the powder material are detected. The foreign substance inspection apparatus 1 comprises a rotatably supported container 5 with an opening surface in a substantially horizontal state; a liftably supported lift member 7 inside the container; a drive control device for controlling rotation of the container 5 and rise and fall of the lift member 7; and a scraping plate 25 disposed on the opening surface 3 of the container 5. The two-dimensional camera 17 is located so as to obtain images of the surface of the powder material that is exposed on the opening surface 3.

7 Claims, 5 Drawing Sheets

FOREIGN SUBSTANCE INSPECTION APPARATUS

FIELD OF THE INVENTION

The present invention relates to an inspection apparatus which detects foreign substances in various powder materials such as medical products, food products and the like.

BACKGROUND OF THE INVENTION

Inspection apparatus which inspects foreign substances mixed into powder materials have been proposed in the fields of medical products and food products by, for example, Japanese Examined Patent Application No. 48065/1995. As shown in FIG. 5, an apparatus 101 oscillates powder material P discharged from a hopper 103 with an oscillating plate 105, to supply a predetermined amount of the powder material P to a belt conveyor 107. A squeezee 109 arranged at the conveyor 107 scrapes the surface of the powder material P, to level the thickness of the powder material P. Thus, images of the powder material P having uniform thickness are obtained with a two-dimensional camera 111. The obtained images are subjected to image processing utilizing brightness differences, whereby foreign substances mixed into the powder material P are detected.

For more accurate inspection with the above-described apparatus, the space between the conveyor 107 and the squeezee 109 is minimized so as to reduce the thickness of the powder material P. However, the narrowed space between the conveyor 107 and the squeezee 109 adversely causes clogging of the powder material P.

The amount of the powder material P supplied to the conveyor 107 and conveying speed of the conveyor 107 should be adjusted in a well-balanced manner in order to supply a predetermined amount of the powder material P to the conveyor 107. Though, when the thickness of the powder material P is reduced, this adjustment becomes difficult, making it difficult to keep the supply amount of the powder material P fixed. The conveying speed of the conveyor 107 is a major factor in the clogging of the powder material P, making it difficult to control the supply amount of the powder material P. Thus, it was difficult to obtain uniform thickness in the powder material on the conveyor, which made it difficult to uniformly level the powder material surface to be inspected.

The present invention has been developed to solve the above-described problems. An objective of the present invention is to provide a foreign substance inspection apparatus with high operating reliability which enables highly-accurate inspection of the intermixing of foreign substances.

DISCLOSURE OF THE PRESENT INVENTION

The objective of the present invention can be achieved by a foreign substance inspection apparatus comprising: a rotatably supported container with an opening surface in a substantially horizontal state; a liftably supported lift member inside the container; a drive control device for controlling rotation of the container and rise and fall of the lift member; a scraping member provided with a scraping part and disposed on the opening surface of the container; and an imaging device for obtaining images of powder material contained in the container. The foreign substance inspection apparatus is configured so that the powder material contained in the container is pushed upward with the rise of the lift member so as to be scraped with the scraping member, and the imaging device is located so as to obtain images of the powder material that is exposed on the opening surface, image data outputted from the imaging device are subjected to image processing. Thus foreign substances mixed into the powder material are detected.

By rotating the container and the lift member in this configuration, the powder material rotates while exposing its surface via the opening surface, and obtains images of the surface of the rotating powder material are obtained with an imaging device. Subsequently, the lift member can be raised to push the powder material upward, so that the surface of the powder material is lifted above the opening surface and the surface of the powder material can be scraped. This scraping operation consecutively produces new imaging surfaces and also levels the powder material surface. As described above, the present invention is different from the prior art, which passes the powder material through a narrow space to level its surface. Therefore, the present invention can prevent the powder material from clogging, which interferes with inspections and thus improves the reliability of the apparatus.

By simply controlling the lifting speed of the lift member, the amount of powder material to be scraped can be controlled, which facilitates the thickness adjustment of the powder material to be viewed. Accordingly, the powder material amount to be scraped can be fixed with high accuracy, and inspection accuracy can be improved.

The foreign substance inspection apparatus of the present invention is further provided with a feed screw rod which threads with the lift member. In the foreign substance inspection apparatus, the drive control device is provided with a driving unit for rotating the container at a predetermined speed of rotation and a transmitting unit for transmitting rotation of the container to the lift member. Preferably, the lift member rotates together with the container so as to rise and fall along the feed screw rod. More preferably, the feed screw rod is configured to be rotatably driven at a predetermined difference in speed of rotation between the feed screw rod and the lift member.

In the foreign substance inspection apparatus, the lift member is preferably supported in the container from above.

In the foreign substance inspection apparatus, it is preferable that the powder material is contained in a ring-shaped region provided in the container and the imaging device is disposed above the region.

In the foreign substance inspection apparatus, it is preferable that a bottom surface of the container is closed and the lift member is supported in the container from above.

BEST EMBODIMENT FOR CARRYING OUT THE PRESENT INVENTION (Embodiment 1)

Figure 1:
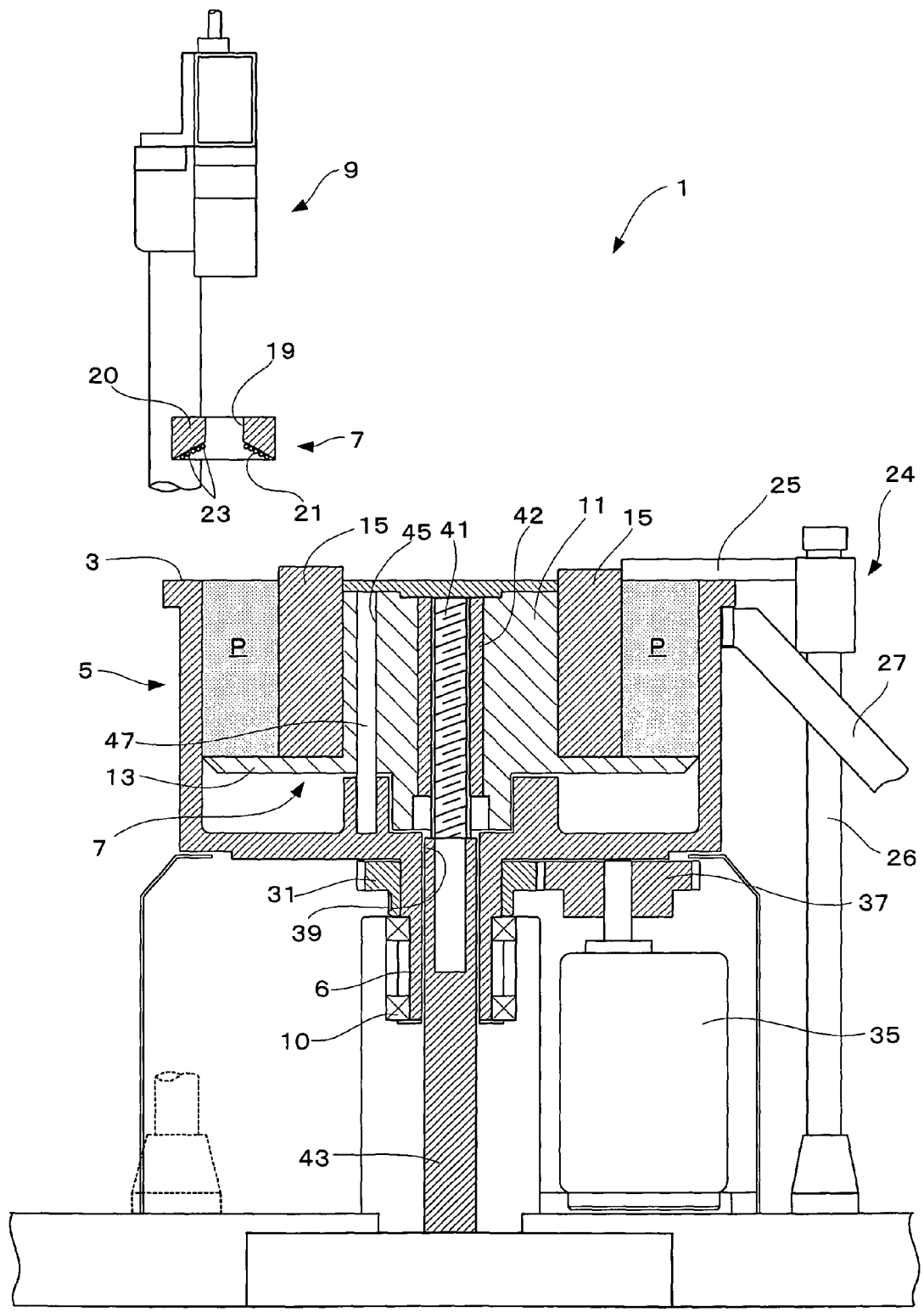
FIG. 1 is an elevational cross-section view illustrating a foreign substance inspection apparatus according to Embodiment 1 of the present invention.
Figure 2:
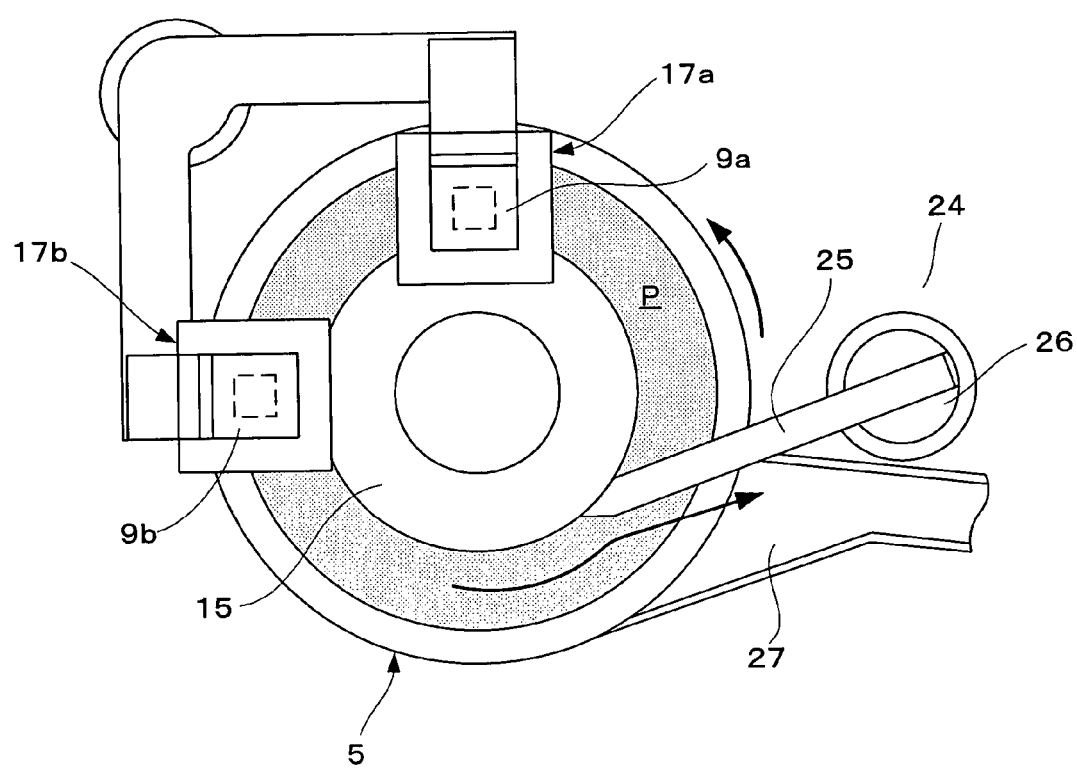
FIG. 2 is a plan view illustrating the apparatus shown in FIG. 1.

Hereinafter, a foreign substance inspection apparatus according to the present invention will be described according to Embodiment 1 with reference to the drawings. FIG. 1 is an elevational cross-section view illustrating a foreign substance inspection apparatus according to the present Embodiment. FIG. 2 is a plan view illustrating the apparatus shown in FIG. 1.

According to the foreign substance inspection apparatus of the present Embodiment, images of various powder materials, such as medical products, food products and the like, are obtained with a camera, and the obtained image data of such powder materials are subjected to image processing. Thus, foreign substances mixed into the powder material are detected. As shown in FIG. 1, the foreign substance inspection apparatus 1 is provided with a container 5 formed in a cup-like shape with a circular plan view which contains the powder material P to be inspected, and a lift member 7 located within the container 5 which raises and lowers the powder material P. A camera 9 for imaging powder materials is disposed above the container 5 and obtains images of the powder material P surface that is exposed via an opening surface 3 of the container 5 from above.

The container 5 is provided at the under surface of the bottom with a boss 6 extending in a substantially vertical direction. A bearing 10 is engaged with the lower portion of the boss 6. The container 5 is supported rotatably via the bearing 10 with an opening surface 3 in a substantially horizontal state. The lift member 7 is provided with an axis part 11 extending in a substantially vertical direction and a ring-shaped part 13 extending from an outer circumference surface of the axis part 11 in a radial direction, on which the powder material P is placed. The lift member 7 is supported liftably in the container 5. The outer diameter of the ring-shaped part 13 is approximately the same size as the inner diameter of the container 5. Thus, the lift member 7 rises and falls creating almost no gap in the container 5.

An annular ring member 15 is detachably arranged on the ring-shaped part 13 of the lift member 7. The powder material P to be inspected is contained in a ring-shaped region provided between the ring member 15 and the inner surface of the container 5. The powder material P thus contained rotates with the container 5 by a drive control device, which will be described later. More specifically, the powder material P moves along a ring-shaped path around the axis part 11. The outer diameter of the ring member 15 may vary, thus making it possible to change the width in the radial direction of the ring-shaped part in which the powder material is contained.

As shown in FIGS. 1 and 2, two conventional two-dimensional cameras 9 (imaging devices) for obtaining images of the powder material P are provided above the container. The cameras 9a and 9b are disposed on the ring-shaped path. A first camera 9a is disposed near the center of the container 5, while a second camera 9b is disposed at a location that is shifted from the first camera 9a by 90? in the radial direction at the downstream side and near the outer circumference of the container 5. The first camera 9a thus obtains images of the powder material P which moves along the inner side of the radial direction, while the second camera 9b obtains images of the powder material P which moves along the outer side of the radial direction. This allows images of the powder material P to be obtained over the entire width in the radial direction. When the width of the powder material is broad, more than two cameras can be used.

As shown in FIG. 1, lighting devices 17a and 17b (FIG. 1 shows only one lighting device) are disposed between the cameras 9a and 9b and the container 5. Each lighting device 17 is provided with a body 20 on which an annular bore 19 is formed. At the bottom of the body 20 is formed a tapered face 21 expanding from the lower end of the bore 19 in a skirt-like form. A plurality of lighting sources 23 are disposed on the tapered face 21. The apparatus is configured so that the lighting sources 23 emit light to the powder material P surface, and then the reflected light enters the cameras 9 via the bore 19, whereby images of a predetermined surface area of the powder material P are obtained by each of the cameras 9 via the bore 19. The obtained images of the powder material P are outputted from the cameras 9 to a conventional image processing device (not shown) and subjected to image processing.

The image processing is conducted as described below. When foreign substances having a color tone which is different from the powder material P are contained in the powder material P, the foreign substances appear as variations in lightness and brightness in the inputted image, thereby allowing foreign substances to be detected. The image processing method is not particularly limited to the above-described method, and any method can be adopted as long as foreign substances in the powder material can be detected. The above-described method employs two-dimensional cameras, but the camera is not limited thereto. More specifically, any camera can be used without particular limitation as long as the camera can obtain images which can be subjected to image processing for the detection of foreign substances. For example, a one-dimensional camera can be used. When using a one-dimensional camera, it is preferable to arrange a plurality of one-dimensional cameras in a straight line in the radial direction so that images of the powder material can be obtained over the entire width of the powder material in the radial direction.

As shown in FIG. 2, a scraper (scraping device) 24 for scraping the powder material P is provided downstream from the second camera 9b located above the container 5. The scraper 24 is composed of a scraping plate (scraping part) 25 disposed on the opening surface 3 of the container 5 and a support 26 for supporting the scraping plate 25. The scraping plate 25 is disposed so as to extend across the powder material P contained in the container 5. The end of the scraping plate 25 makes contact with the outer circumference of the ring member 15 and extends from the ring member 15 substantially vertically in the rotation direction of the container 5. The underside of the scraping plate 25 makes contact with the upper surface of the outer circumference wall of the container 5. Thus, the scraping plate 25 scrapes the amount of the powder material P surface that is above the opening surface 3 of the container 5, which will be described later. The scraped powder material P is collected from a chute 27 attached to the outer circumference wall of the container 5 under the scraping plate 25.

A drive control device which drives the container 5 and the lift member 7 is configured as described below. As shown in FIG. 1, a first gear 31 is fixed to the upper portion of the boss 6 formed on the bottom of the container 5, that is, above the bearing 10. The first gear 31 is engaged with a second gear 37 which is rotatably driven with a motor (driving unit) 35.

A bore 39 that communicates with the boss 6 is provided at the bottom center of the container 5, through which a feed screw rod 41 extends in a substantially vertical direction. The feed screw rod 41 is provided with male threads on the outer circumference face. The feed screw rod 41 threads with a female thread part 42 which is formed at the axis part 11 of the lift member 7. The lower portion thereof is fixed to the axis body 43 which is inserted into the boss 6. The axis body 43 is fixed at the bottom of the foreign substance inspection apparatus 1. A rod-shaped member (transmission unit) 47 is disposed at a location shifted from the center of the bottom of the container 5 and extends substantially vertically in the upward direction. The rod-shaped member 47 is inserted slidably through a vertical bore 45 formed in the axis part 11 of the lift member 7.

The drive of the motor 35 rotates the container 5 via the first and second gears 31 and 37, while also rotating the lift member 7 in an integrated manner with the container 5 by means of the rod-shaped member 47. The lift member 7 threads with the feed screw rod 41 and thus moves vertically while rotating with the container 5. The speed of rotation of the container 5 varies depending on the properties of the powder material P to be inspected, the camera performance, etc., but any speed of rotation is acceptable as long as images of moving powder material P can be obtained. For example, the speed of rotation can be set to 1 to 60 rpm.

Next, the operation of the foreign substance inspection apparatus 1 thus configured will be described. Initially, as shown in FIG. 1, the lift member 7 is lowered to a point near the bottom of the container 5. The powder material P to be inspected is then poured into the container 5. At this time, the powder material P is placed in a ring-like shape on the lift member 7. Subsequently, the opening surface 3 is closed with a flat lid member (not shown), and the lift member 7 is then raised. The powder material P is thus compressed between the ring-shaped part 13 of the lift member 7 and the lid member, which makes it possible to crush any lumps and eliminate any air included in the powder material P, to give the powder material P a uniform density.

The lid member is then removed, and the motor 35 is driven, thereby rotating the container 5 via the first and second gears 31 and 37, and at the same time rotating the lift member 7 together with the container 5. The rotation causes the lift member 7 to rise on the feed screw rod 41. Accordingly, the powder material P on the lift member 7 is pushed upward while rotating.

As shown in FIG. 2, rotation of the container 5 causes the powder material P to move along a ring-shaped path, and thus images of the rotating powder material P can be obtained at two points with the two-dimensional cameras 9$a$ and 9$b$ disposed on the ring-shaped path. The time intervals for obtaining these images can be set as desired. For example, when the container 5 rotates at 15 rpm, images can be obtained once per second. Because the powder material P is pushed up while rotating, the amount that rises above the opening surface 3 of the container 5 after passing by the two-dimensional camera 9 is scraped with the scraping plate 25. The scraped powder material P passes over the outer wall of the container 5 along the edge of the scraping plate 25 and flows into a chute 27. Thus, the powder material P is scraped by a predetermined amount with every rotation of the container 5, which successively produces new surface to be obtained as an image. Thus, the inspection of foreign substances in the powder material P can be done continuously. The volume of the powder material to be inspected by each imaging operation is calculated as follows: image area ? amount of powder material that rises per rotation, and any foreign substances in this volume of powder material P will be detected.

According to the above-described image processing with the cameras 9, only the images of the surface layer of the powder material P are obtained, so it is preferable to reduce thickness of the powder material P being viewed as much as possible to achieve an accurate inspection of foreign substances. In order to do this, the lifting speed of the lift member 7 should be reduced as much as possible. For example, it is preferable to set the rise of the lift member 7 to 0.05 to 5 mm per rotation. When the image area to be obtained with the two-dimensional cameras 9 is set to 15 cm$^2$ and the rise of the lift member 7 is set to 0.2 mm per rotation, each imaging operation permits the inspection of foreign substances in a volume of 0.3 cm$^3$ of powder material.

As described above, according to the present Embodiment, the rotation of the container 5 and the lift member 7 causes the powder material P to rotate while exposing its surface layer via the opening surface 3, so that the images of the surface layer of the powder material are obtained with the two-dimensional cameras 9. Subsequently, the rise of the lift member 7 pushes the powder material P upward, so that the amount of the powder material P surface that rises above the opening surface 3 is scraped, thus successively producing new surfaces as images to be obtained and also leveling the powder material P surface. As described above, the present invention is different from the prior art, which passes the powder material through a narrow space so as to level the powder material surface. Therefore, the present invention can avoid the clogging of powder material which interferes with the inspection process and thus improve the reliability of the apparatus.

Also, because the amount of the powder material P to be scraped can be controlled by simply controlling the lifting speed of the lift member 7, the thickness of the powder material P to be obtained as an image can be easily regulated. In particular, the lift member 7 is lifted with high accuracy in the present Embodiment, because the feed screw rod 41 is employed. More specifically, the lifting speed of the lift member 7 can be automatically fixed by fixing speed of rotation of the lift member 7. Accordingly, the powder material P amount to be scraped can be fixed with high accuracy, and thus the inspection accuracy can be further improved.

Also, only the inside of the container 5 of the foreign substance inspection apparatus 1 needs to be cleaned, which facilitates and speeds up the cleaning process, compared to the prior art which requires cleaning of a hopper and conveyor.

Moreover, a conventional apparatus needs to be provided with a conveyor for transmitting the powder material in a straight line, which requires a large installation space for the apparatus. In contrast, the foreign substance inspection apparatus according to the present Embodiment inspects foreign substances while rotating the powder material P in the container 5, so only the space for the container 5 is necessary, which reduces the space needed for installing the apparatus.

To further raise the inspection accuracy, the lifting speed of the lift member 7 should be reduced so as to minimize the thickness of the powder material to be inspected with each imaging operation, which requires a reduction in the pitch of the feed screw rod 41 and the female thread part 42. However, reducing this pitch would lower the mechanical strength. Moreover, the necessary processing would also be difficult. Thus, when the drive control device is configured as described below, the lifting speed can be reduced without lowering the mechanical strength.

(Embodiment 2)

Figure 3:
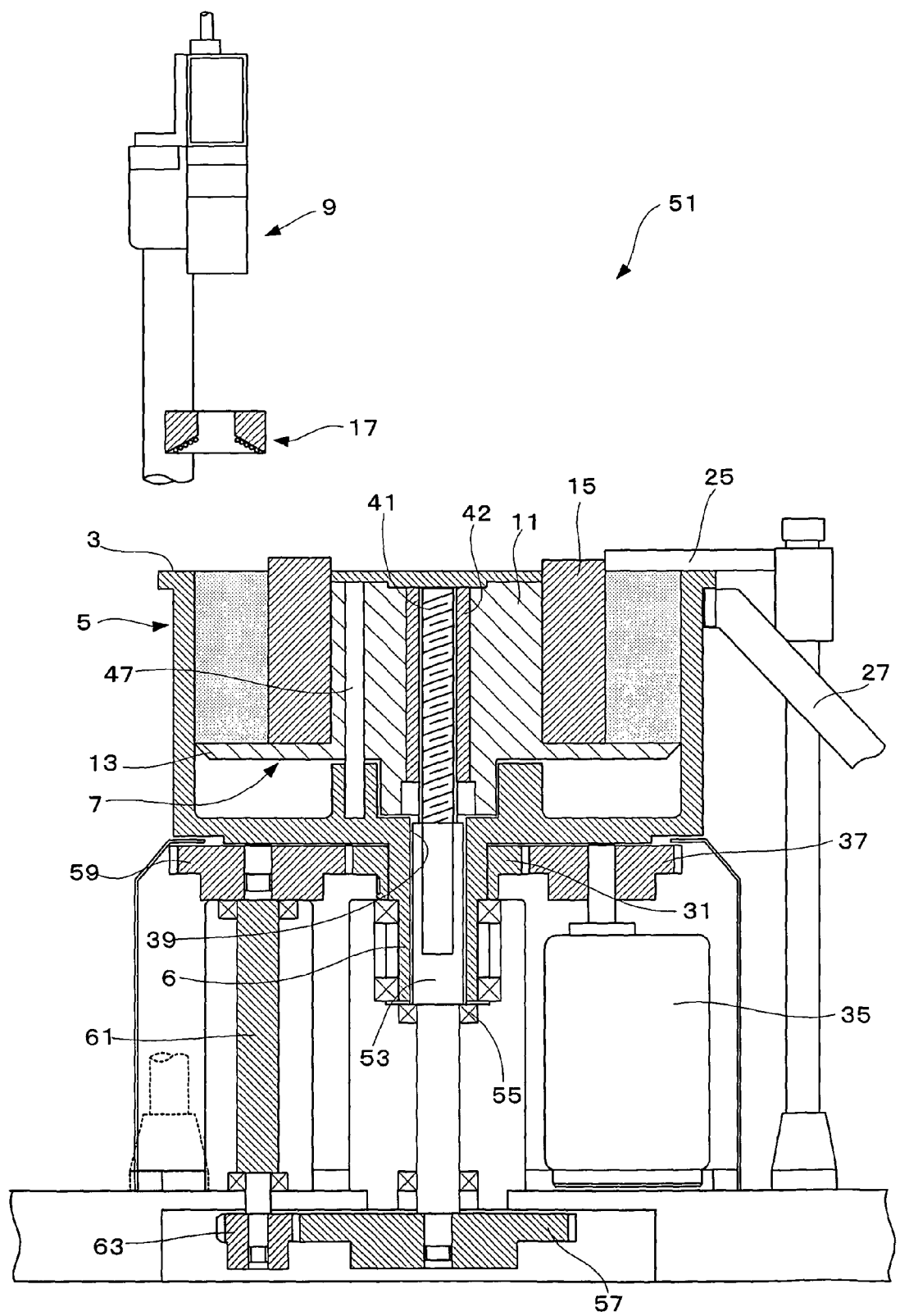
FIG. 3 is an elevational cross-section view illustrating a foreign substance inspection apparatus according to Embodiment 2 of the present invention.

The foreign substance inspection apparatus of the present invention will next be described according to Embodiment 2 with reference to the drawings. FIG. 3 is an elevational cross-section view of the foreign substance inspection apparatus according to the present Embodiment. The foreign substance inspection apparatus according to the present Embodiment is different from the apparatus according to Embodiment 1 only in the drive control device, and the remaining configuration is the same as in the apparatus according to Embodiment 1. Therefore, the same parts are designated by the same numerals and the descriptions are omitted.

As shown in FIG. 3, a drive control device for a foreign substance inspection apparatus 51 is configured in such a way as to rotate the feed screw rod 41 around a vertical axis. More specifically, an axis body 53 in which the feed screw rod 41 is held is supported rotatably by a bearing 55 arranged at a lower portion of the boss 6. A third gear 57 is detachably connected to the lower end portion of the axis body 53. A fourth gear 59 to be engaged with the first gear 31 is located at a position opposite to the second gear 37 with the axis body 53 interposed. The fourth gear 59 is attached to an axis body 61 that is supported rotatably and extending downwardly. A fifth gear 63 to be engaged with the third gear 57 is detachably attached to the lower end portion of an axis member 61. In the present Embodiment, the number of teeth on the fourth gear 59 is the same as that on the second gear 37, while the number of teeth on the third gear 57 is greater than that on the fifth gear 63. Accordingly, the rotation of the container 5 is transmitted to the feed screw rod 41 at a speed that is reduced by these gear mechanisms.

According to the above configuration, the reduced speed of rotation caused by the third and fifth gears 57 and 63 causes the feed screw rod 41 to rotate more slowly than the container 5. Therefore, difference in the speed of rotation between the container 5 and the feed screw rod 41 is equal to the speed of rotation of the lift member 7 relative to the feed screw rod 41. For example, when the speed of rotation of the motor 35 is set similarly to that in Embodiment 1, the lifting speed of the lift member 7 is reduced. Thus, even if the pitch of the feed screw rod 41 and the female thread part 42 is increased, the lifting speed of the lift member 7 can be kept low. As described above, the pitch of the thread can be increased, thereby providing high mechanical strength and improved apparatus reliability. The feed screw rod 41 and the female thread part 42 can be easily processed.

The third and fifth gears 57 and 63 are readily detachable. Therefore, replacing these gears allows the feed screw rod 41 to rotate at the desired reduced speed of rotation. This allows the lifting speed of the lift member 7 to be suitably varied.

The configuration for rotating the feed screw rod 41 is not limited to the above. Any configuration is acceptable as long as the feed screw rod 41 is rotatably driven at a predetermined difference in speed of rotation between the container 5 and the feed screw rod 41 and the lifting speed of the lift member 7 can be reduced. For example, another motor can be separately provided in addition to the motor 35 for rotating the container 5 so that the feed screw rod 41 can be rotated. In this case, the speed of rotation of the feed screw rod 41 can be suitably varied to change the lifting speed of the lift member 7.

According to the foreign substance inspection apparatus described in each of the above Embodiments, the space between the outer circumference of the lift member 7 and the inner wall surface of the container 5 cannot be completely eliminated. Thus, the powder material P sometimes passes through this space and accumulates at the bottom of the container 5. In the present Embodiment, a bore 39 is formed at the bottom center of the container 5, and thus the powder material P accumulating at the bottom of the container 5 sometimes falls downward through the bore 39. The fallen powder material P may interfere with the operation of the gears and motors disposed below the container 5. A drive control device configured as described below can solve the above-described problem.

(Embodiment 3)

Figure 4:
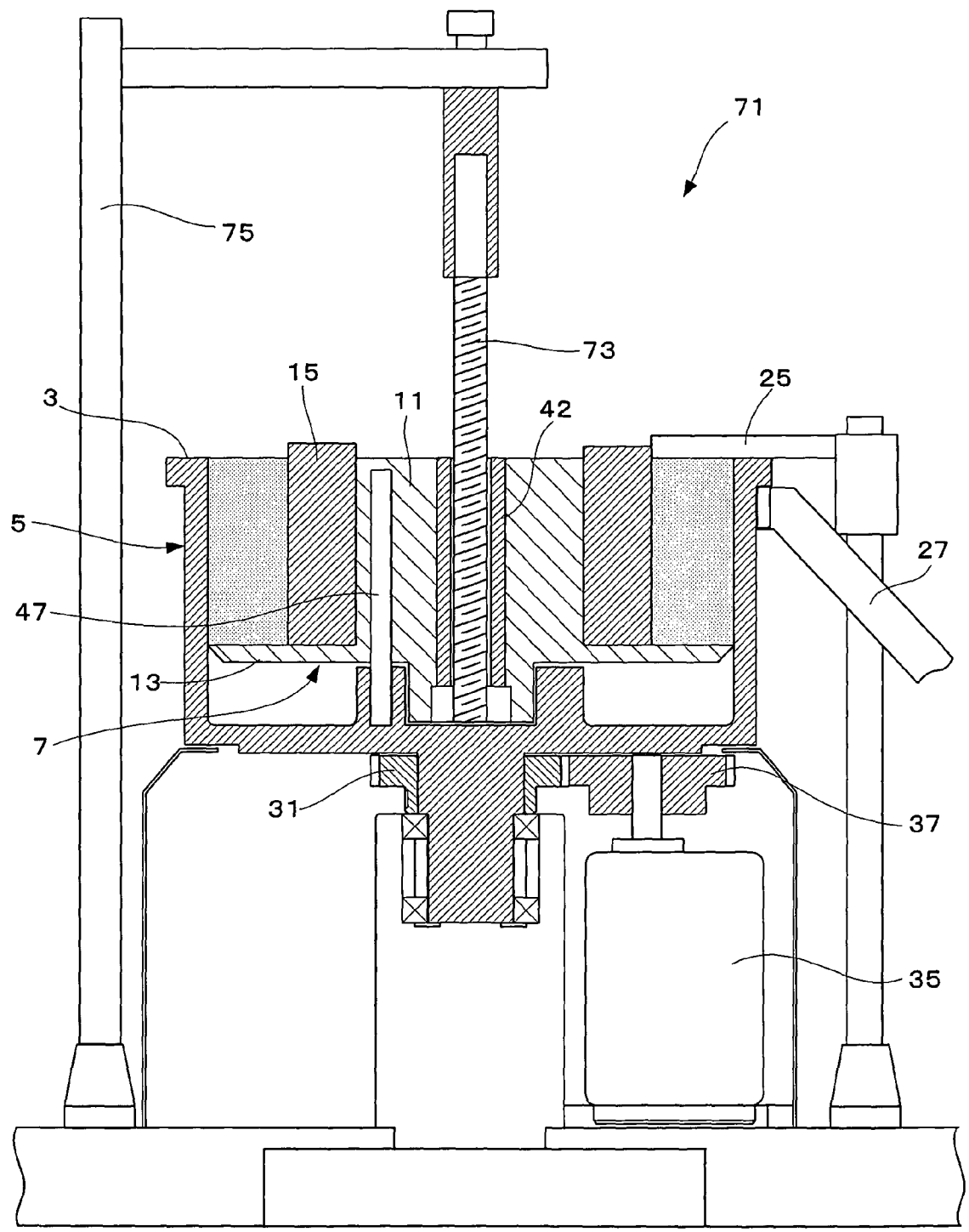
FIG. 4 is an elevational cross-section view illustrating a foreign substance inspection apparatus according to Embodiment 3 of the present invention.
Figure 5:
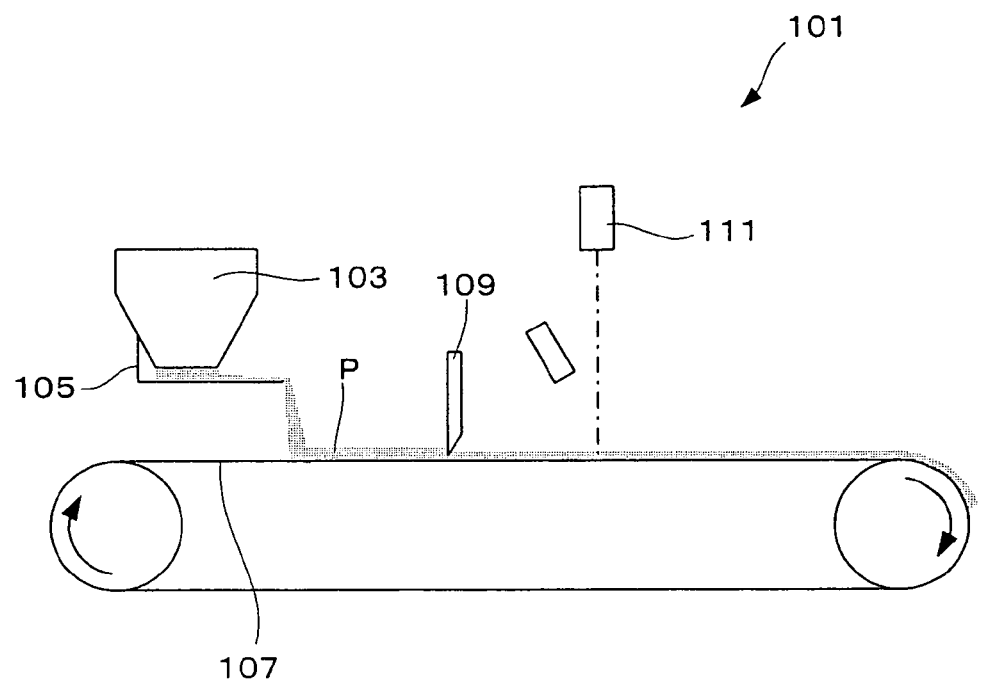
FIG. 5 is an elevation view illustrating a prior art foreign substance inspection apparatus.

Next, a foreign substance inspection apparatus of the present invention will be described according to Embodiment 3 with reference to the drawings. FIG. 4 is an elevational cross-section view illustrating a foreign substance inspection apparatus according to the present Embodiment. The foreign substance inspection apparatus according to the present Embodiment is different from that according to Embodiment 1 in the configuration of the container and the drive control device. The remaining configuration is the same as that in Embodiment 1, and thus, the same parts are designated by the same numerals and the descriptions are omitted. In FIG. 4, the cameras and the lighting device are not shown.

As shown in the drive control device of a foreign substance inspection apparatus 71 of FIG. 4, a feed screw rod 73 for raising and lowering the lift member 7 is supported by a support 75 in such a way that it is suspended over the axis part 11 of the lift member 7. The feed screw rod 73 is configured to thread with the female thread part 42 of the axis part 11. The feed screw rod 73 threads with the lift member 7 from above, and thus there is no bore 39 provided in the bottom of the container 5 (see FIG. 1) for the feed screw rod to extend through as in Embodiment 1.

Also in this configuration, when the lift member 7 rotates with the container 5, the lift member 7 rises due to the feed screw rod 73 in the same manner as in Embodiment 1.

According to the present Embodiment, the feed screw rod 73 supports the lift member 7 from above. Because no bore is provided at the bottom of the container 5 for the feed screw rod to extend through, this configuration can prevent the powder material P that flows from the lift member 7 to the bottom of the container 5 from flowing to the outside of the container 5. Therefore, the present invention can prevent powder material from adhering to the gears 31, 37 and the motor 35 for rotating the container 5, thereby preventing a malfunction from occurring in the apparatus.

In the present Embodiment, the feed screw rod 73 is fixed, but it may be configured to rotate as in Embodiment 2. Thus, under the condition where the lifting speed of the lift member 7 is kept low, the pitch of the feed screw rod 73 and the female thread part 42 can be increased. The feed screw rod 73 can be rotated with, for example, another motor which is different from the motor for rotating the container 5, or a gear can be used to transmit rotation of the container 5 at a reduced speed.

As described above, the present invention has been described with reference to several Embodiments thereof, but it is not limited thereto, and various modifications can be readily made without departing from the scope and spirit of the present invention.

In each of the above Embodiments, the rod-shaped member 47 is provided inside the container 5, and is configured to slide with the axis part 11 of the lift member 7, but the configuration is not limited thereto as long as the rotation of the container 5 can be transmitted to the lift member 7. For example, the inner wall surface of the container 5 can be provided with a key extending vertically, and a key groove capable of engaging with such a key can be formed on the outer circumference of the lift member 7. This configuration will also cause the lift member 7 to rotate together with the container 5 and rise in the same manner as that in each of the above Embodiments.

Each of the above Embodiments employs a configuration such that the common motor 35 rotates the container 5 and the lift member 7 and causes the lift member 7 to rise. However, it can be configured that the rotation and the rise can be operated by separate motors. More specifically, a driving unit for rotating the container and a driving unit for raising and lowering the lift member can be separately provided. A mechanism such as a rack and pinion can also be used to raise and lower the lift member 7.

What is claimed is:

1. A foreign substance inspection apparatus comprising:
   a rotatably supported container with an opening surface in a substantially horizontal state;
   a liftably supported lift member inside the container;
   a drive control device for controlling rotation of the container and rise and fall of the lift member;
   a scraping member provided with a scraping part and disposed on the opening surface of the container and
   an imaging device for obtaining images of powder material contained in the container,
   wherein the powder material contained in the container is pushed upward with the rise of the lift member so as to be scraped with the scraping member,
   the imaging device is located so as to obtain images of the surface of the powder material that is exposed on the opening surface and
   image data outputted from the imaging device are subjected to image processing, whereby foreign substances mixed into the powder material are detected.

2. The foreign substance inspection apparatus according to claim 1, wherein the lift member rotates together with the container.

3. The foreign substance inspection apparatus according to claim 1,
   wherein the powder material is contained in a ring-shaped region provided in the container and
   the imaging device is disposed above the region.

4. The foreign substance inspection apparatus according to claim 1 further comprising:
   a feed screw rod which threads with the lift member,
   wherein the drive control device is provided with a driving unit for rotating the container at a predetermined speed of rotation and a transmitting member for transmitting the rotation of the container to the lift member, and
   the lift member rotates together with the container so as to rise and fall along the feed screw rod.

5. The foreign substance inspection apparatus according to claim 4, wherein the feed screw rod is configured to be rotatably driven at a predetermined difference in speed of rotation between the feed screw rod and the lift member.

6. The foreign substance inspection apparatus according to claim 1, wherein the lift member is supported in the container from above.

7. The foreign substance inspection apparatus according to claim 1,
   wherein a bottom surface of the container is closed and the lift member is supported in the container from above.

* * * * *